United States Patent
Peters

(10) Patent No.: US 12,280,345 B2
(45) Date of Patent: Apr. 22, 2025

(54) CONTAINER AND METHOD FOR INSTALLING AN AGITATOR IN A CONTAINER

(71) Applicant: Jean-Marc Peters, Eupen (BE)

(72) Inventor: Jean-Marc Peters, Eupen (BE)

( * ) Notice: Subject to any disclaimer, the term of this patent is extended or adjusted under 35 U.S.C. 154(b) by 962 days.

(21) Appl. No.: 17/352,310

(22) Filed: Jun. 20, 2021

(65) Prior Publication Data
US 2021/0370247 A1 Dec. 2, 2021

Related U.S. Application Data

(63) Continuation of application No. PCT/EP2019/086563, filed on Dec. 20, 2019.

(30) Foreign Application Priority Data

Dec. 20, 2018 (DE) .......................... 102018133226.2

(51) Int. Cl.
| | | |
|---|---|---|
| *B01F 7/00* | (2006.01) | |
| *B01F 7/02* | (2006.01) | |
| *B01F 7/04* | (2006.01) | |
| *B01F 15/00* | (2006.01) | |
| *B01F 27/072* | (2022.01) | |

(Continued)

(52) U.S. Cl.
CPC .......... *B01F 27/61* (2022.01); *B01F 27/0722* (2022.01); *B01F 27/0726* (2022.01); *B01F 27/1125* (2022.01); *B01F 27/191* (2022.01); *B01F 27/70* (2022.01); *B01F 35/10* (2022.01); *B01F 35/4121* (2022.01); *C12M 21/04* (2013.01); *C12M 27/06* (2013.01); *B01F 2215/0422* (2013.01)

(58) Field of Classification Search
CPC .................. B01F 27/61; B01F 27/0722; B01F 27/0726; B01F 27/1125; B01F 27/191; B01F 27/70; B01F 35/10; B01F 35/4121; B01F 2215/0422; B01F 27/906; C12M 21/04; C12M 27/06; Y02W 30/40

See application file for complete search history.

(56) References Cited

U.S. PATENT DOCUMENTS

| | | | | |
|---|---|---|---|---|
| 1,778,049 A | * | 10/1930 | Thornton ................. | B01F 27/86 241/3 |
| 2015/0093811 A1 | * | 4/2015 | Peters .................... | C12M 27/06 435/283.1 |

FOREIGN PATENT DOCUMENTS

| | | | |
|---|---|---|---|
| DE | 202004012236 U1 * | 12/2004 | ........ B01F 15/00701 |
| DE | 102004027077 A1 | 1/2006 | |

(Continued)

*Primary Examiner* — Liban M Hassan
(74) *Attorney, Agent, or Firm* — Von Rohrscheidt Patents

(57) ABSTRACT

A container for fermenting bio-degradable substances, the container comprising: a base and a wall, wherein an interior of the container is enclosed by the base and the wall; a rotatable agitator that protrudes into the interior and is supported in an upper bearing and a lower bearing in an installed position of the rotatable agitator in the container, wherein the rotatable agitator includes a shaft that is drivable by a drive, wherein at least one stirring paddle is arranged at the shaft and configured to co-rotate with the shaft so that substances arranged in the container are stirrable, wherein the lower bearing is arranged at the at least one base of the container and a bearing device located at a lower end of the shaft is supported in the lower bearing in the installed position of the rotatable agitator.

8 Claims, 3 Drawing Sheets

(51) Int. Cl.
*B01F 27/1125* (2022.01)
*B01F 27/191* (2022.01)
*B01F 27/61* (2022.01)
*B01F 27/70* (2022.01)
*B01F 35/10* (2022.01)
*B01F 35/41* (2022.01)
*C12M 1/06* (2006.01)
*C12M 1/107* (2006.01)

(56) References Cited

FOREIGN PATENT DOCUMENTS

| | | | | |
|---|---|---|---|---|
| DE | 202008010638 U1 | | 11/2008 | |
| DE | 202010015332 U1 | * | 3/2011 | ............. A01C 3/026 |
| DE | 102011114793 A1 | * | 4/2012 | ........ B01F 15/00006 |
| DE | 102011055312 A1 | | 5/2013 | |
| DE | 102013219938 A1 | | 4/2015 | |
| JP | 2004305968 A | * | 11/2004 | |

\* cited by examiner

CONTAINER AND METHOD FOR INSTALLING AN AGITATOR IN A CONTAINER

RELATED APPLICATIONS

This application is a continuation of International Application PCT/EP2019/086563 filed on Dec. 20, 2019 claiming priority from German patent application DE 10 2018 133 226.2 filed on Dec. 20, 2018, both of which are incorporated in their entirety by this reference.

FIELD OF THE INVENTION

The invention relates to a container, in particular a fermenter for fermenting biologically degradable substances. The invention furthermore relates to a method for installing a rotatable agitator in a container.

BACKGROUND OF THE INVENTION

Containers of the type describe supra like the fermenters, are well known in the art and are used in particular in biogas plants that are used for renewable energy production. Containers with agitators that are arranged at a slant angle have the advantage that the substrate arranged in the container is mixed in a horizontal as well as in a vertical direction so that an undesirable de-mixing of the substrate into individual layers that impedes the fermentation process is prevented.

Rotatable agitators are subject to normal wear during operations in particular in bearings and in the transmission of the rotatable agitator. Depending on the quality of the rotatable agitator the rotatable agitator will fail sooner or later due to a failure of at least one of the wear components. The wear components then have to be replaced in order to put the rotatable agitator back in service. In fermenters with a plurality of rotatable agitators a temporary failure of an individual agitator is tolerable for a certain time. The reduced circulation of the substrate that is arranged in the fermenter, however, slows the biological decomposition process down which eventually leads to a reduction of the throughput and to a reduction of the energy output of the biogas plant. This significantly reduces the economic viability of the biogas plant. Therefore, a long term shut down of one or plural rotatable agitators is not acceptable.

Therefore, the failed rotatable agitators are repaired or replaced. For this purpose, it is typically required to open and empty the fermenter and to shut the biogas plant down. These shut down times are expensive and undesirable.

DE10 2004 027 077A1 discloses a rotatable agitator for a fermenter including an inclined shaft that is heatable. The shaft is supported in a flexible upper shaft bearing that is arranged in an upper portion of the fermenter wall and a lower shaft bearing that facilitates variably adjusting the inclination angle during assembly and pivoting the bearing relative to a mounting block in order to be able to compensate for dimensional tolerances during mounting of the shaft. It is a disadvantage of the known rotatable agitator that the entire filling height of the fermenter is not available during operations since a filling of the fermenter is only possible up to the upper shaft bearing. The flexible shaft bearings are failure prone as well.

Another rotatable agitator with an agitator shaft that is arranged at a slant angle can be derived from DE 10 2013 219 938 A1. The described agitator is characterized in that the upper shaft bearing is supported at a top side of the fermenter wall. When mounting the rotatable agitator it is moved from a vertical orientation into an inclined operating position by moving a bearing that is arranged at a lower end of the shaft along a support device that is arranged at the base of the fermenter.

When the rotatable agitators are exclusively supported at the container wall there is a problem in large size fermenters in that a center portion of the fermenter is not reached by the rotatable agitators any more so that there is no sufficient mixing. This, however, greatly reduces the performance of the plant.

In the rotatable agitator disclosed in DE 20 2004 004 101 U1, a lower end of the shaft is supported in a base bearing and an upper end of the shaft is supported in a service shaft that is arranged laterally adjacent to the fermenter container. In the installed position the shaft is inclined by approximately 45° relative to horizontal. In order to facilitated disassembly of the agitator the agitator paddles are movable from an operating position where they are angled away from an axis of the shaft into a mounting position where they are folded proximal to the stirring shaft which significantly reduces an outer diameter of the entire rotatable agitator. Fixing the paddles in the operating position or disengaging the paddles from the operating position is performed by an adjustment device that is arranged at an upper end of the shaft and that facilitates actuating a push rod that extends to the agitation paddle attachment locations. The adjustment device for the paddle fixation makes handling the agitator more difficult since contact with the container wall or other support devices has to be prevented in this area.

DE 20 2004 012 236 U1 discloses a rotatable agitator that is arranged at a slant angle in a fermenter container wherein the rotatable agitator is supported at an upper support console outside of the container and at a lower support console that is arranged in the liquid that is included in the container. During dismounting as well as during mounting of the rotatable agitator the lower end of the shaft is coupled with a search hook or search ring that is connected in turn with a rope that is run out of the container through an opening that is arranged above the base bearing and thus movable. The opening in the container ceiling therefore helps to find the correct position for the lower shaft end when introducing the lower shaft end into the base bearing.

BRIEF SUMMARY OF THE INVENTION

Thus, it is an object of the instant invention to provide a container where the rotatable agitator can be replaced in a simple manner during operations. The invention also relates to a method for installing the rotatable agitator in a container.

The object is achieved by a container for fermenting bio-degradable substances, the container including at least one base and at least one wall, wherein an interior of the container is enclosed by the at least one base and the at least one wall; at least one rotatable agitator that protrudes into the interior and is supported in an upper bearing and a lower bearing in an installed position of the rotatable agitator in the container, wherein the rotatable agitator includes a shaft that is drivable by a drive, wherein at least one stirring paddle is arranged at the shaft and configured to co-rotate with the shaft so that substances arranged in the container are stirrable, wherein the lower bearing is arranged at the at least one base of the container and a bearing device located at a lower end of the shaft is supported in the lower bearing in the installed position of the rotatable agitator, wherein the shaft includes a longitudinal axis which is inclined at an angle between 5 degrees and 60 degrees relative to vertical in the installed position of the rotatable agitator, wherein a guide is arranged at an upper side of the container and includes a contact surface for at least a section of the shaft, and wherein a lower end of the shaft of the rotatable agitator is alignable with the lower bearing into an aligned position of the shaft by moving the shaft along the contact surface so that the rotating actuator is axially movable from the aligned position into the installed position.

The top side of the container is a portion of the container according to the invention that is free from the substance included in the container like e.g. an upper portion or an upper section of the container wall, or a portion of the container ceiling e.g. made from concrete. Thus, the rotatable agitator that is to be newly inserted is not supported in the portion of the lower bearing but at the top side of the container, e.g.; at the wall so that a more precise installed position is achievable also when the container is filled, and the view of the lower bearing is obstructed. The support device can be positioned e.g. at the wall of the container and can predetermine a movement of the rotatable agitator is several ways. The movement can be performed on a direct path to the lower bearing, thus in a straight line or the movement can be piece wise linear or the path can be curved. The support device according to the invention facilitates an insertion of a new or repaired rotatable agitator also when the container is filled wherein the insertion is comfortable for the technicians, in particular since aligning and inserting the rotatable agitator can be performed from outside the container. An aligned condition of the shaft or of the rotatable agitator advantageously is a position in which a longitudinal axis of the shaft coincides with an axis of the lower bearing that is fixed in place. The axial movement of the rotatable agitator or of the shaft at least at an end of the assembly movement by itself facilitates reaching the installation position where the lower end of the shaft engages the lower bearing in a simple and reliable manner.

A section of the shaft that is supported at the contact surface of the support device can be e.g.; an upper section of the shaft itself that is free from stirring elements. Thus, it is conceivable that the rotatable agitator is initially inserted into the container without contacting the support device and that the shaft only contacts the support device when all stirring elements are already arranged in the interior of the container. A correct orientation of the shaft only in the last section of the insertion path is sufficient in order to insert the shaft into the lower bearing and to bring the rotatable agitator into the correct installation position.

Thus, the support device already facilitates an alignment of the rotatable agitator when the lower end of the shaft is still at a certain distance from the lower bearing so that a movement in an aligned condition providing a forced guidance of the shaft is already possible over a sufficiently long distance before the engagement between the lower shaft end and the lower bearing.

Advantageously the support device does not extend into the portion of the container where the materials that are to be agitated are arranged. It is possible, however, that the support device extends partially into the interior of the container.

In an advantageous embodiment of the invention the rotatable agitator includes an extension that is disengageably connected with an upper end of the shaft. Overall the shaft is only extended for the assembly so that the torque that is required for placing the shaft at a slant angle can be applied by hand or by a lifting arrangement. Thus, handling the agitator that is to be inserted is simplified considerably. After the installation position is reached the extension can be removed from the shaft. This way the extension does not protrude beyond a top edge of the container during operations which advantageously reduces installation space requirements. Furthermore the retrieved extension can be used to install an additional rotatable agitator. Furthermore a large distance between the drive (motor-transmission) combination and the cover device is undesirable since supporting the torque then becomes complex.

According to an advantageous embodiment of the invention it is provided that the shaft including the associated extension protrudes beyond a top edge of the wall in an installed position wherein a section of the extended shaft that protrudes beyond the wall has a length of at least 1 m, advantageously at least 2 m. The longer the shaft, typically between approximately between 4 m and 11 m, the longer the extension in order to be able to introduce sufficient torque into the rotatable agitator outside of the container in order to facilitate the slanting that is required for the insertion process into the lower bearing. This way the section of the shaft that does not includes any agitation elements is longer than in conventional rotatable agitators by an amount which corresponds to the protruding section of the shaft. This has the advantage that the shaft can be supported along the support device over an extended length which simplifies handling during assembly and increases precision of the support. The support device can include e.g.; a tube that is cut in the longitudinal direction and has an inner diameter that corresponds to the outer diameter of the shaft or the extension connected therewith, wherein the contact surface forms a partial circle. The tube can be supported in place e.g.; by a tripod that is attached at the wall or at a ceiling of the container. In this case the contact surface is inclined at the same angle relative to vertical as the rotatable agitator in its installed position.

In an advantageous embodiment a longitudinal axis of the extension coincides with the longitudinal axis of the shaft, wherein the extension advantageously has a diameter that corresponds to a diameter of the shaft.

With respect to using the container according to the invention as a fermenter it is advantageous when a sealing device is provided wherein an interior of the container is enveloped essentially gas tight by the base, the wall and the sealing device. The sealing device according to the invention forms the top side of the container or part of the top side of the container that can also be designated an upper section of the container. The ceiling device can be a concrete ceiling or a membrane that is attached at the wall and is pulled tight over the container. A mixed form made from concrete ceiling and membrane or other ceiling devices is also possible.

In particular when the ceiling device is configured as a concrete ceiling there is the advantage that the support device can be positioned on the concrete ceiling so that the rotatable agitators can also be arranged in a center portion of the container. A concrete ceiling provides numerous options to arrange the support device in a stable manner and to anchor the support device so that forces that are generated in the support of the rotatable agitator are reacted in the concrete ceiling. It is appreciated that the concrete ceiling is provided with openings that may be closable in order to facilitate installation, removal and operations of rotatable agitators.

When the container according to the invention includes a ceiling device it is advantageous when the ceiling device includes at least one opening for passing a rotatable agitator through and the support device is arranged at the at least one opening. Thus, it is conceivable that the support device protrudes into the interior of the container.

For operating the rotatable agitator it is particularly advantageous when the support device is connected with the container in a disengageable manner. After installing the rotatable agitator the support device can be removed and the drive including a motor and a transmission can be mounted at the rotatable agitator. The removability of the support device does not cause any competing space requirement of support device and drive.

In an advantageous embodiment the support device includes at least two fixing devices for fixing the at least one section of the shaft at the support device wherein the fixing devices facilitate a linear relative movement between the contact surface and the shaft and wherein the shaft is advantageously aligned with the contact surface in a fixed condition of the shaft. Therefore the shaft can be fixed at the support device in a sliding manner after it has been brought in contact with the support device. Therefore a manual support of the shaft at the support device can be omitted.

The invention also relates to a method for installing a rotatable agitator in a container, in particular in a fermenter where a shaft of the rotatable agitator includes a longitudinal axis which encloses an angle between 5 degrees and 60 degrees in an installed position of the rotatable agitator relative to vertical and where the rotatable agitator is inserted into an inner cavity of the container is achieved, the method including step:

Contacting at least one section of the shaft with a contact surface of a support device that is arranged at the container and aligning a lower end of the shaft with a lower bearing, subsequently moving the shaft along the contact surface until the rotatable agitator is in the installation position. Advantages cited with respect to the container apply analogously to the method according to the invention.

In an advantageous embodiment of the method according to the invention at least one section of the shaft is connected by at least two fixing elements with the support device before the shaft is moved along the contact surface.

It is appreciated that various features of the dependent claims can be implemented by themselves or in any combination in advantageous embodiments of the invention.

BRIEF DESCRIPTION OF THE DRAWINGS

The invention is subsequently described based on an embodiment with reference to drawing figures, wherein.

DETAILED DESCRIPTION OF THE INVENTION

Figure 1:
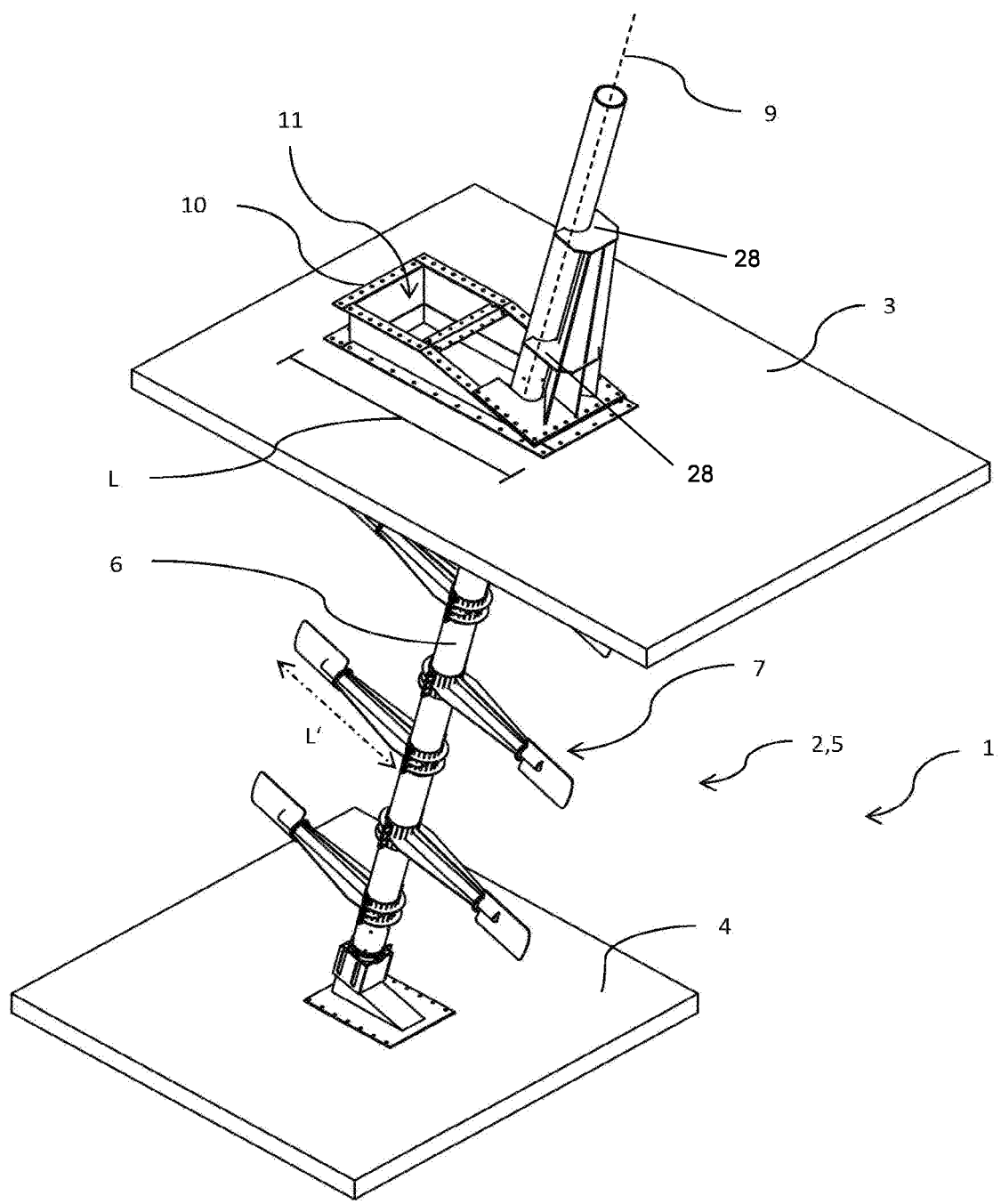
FIG. 1 illustrates a three dimensional view of a container according to the invention.

FIG. 1 illustrates a container 1 according to the invention that is configured as a fermenter and includes a rotatable agitator 2, wherein only a detail of the fermenter is shown for the purposes of clarity. Accordingly only a portion of a ceiling device 3 and a portion of a base configured as a base plate 4 and a portion of a wall 26 are shown. The ceiling device 3, the base plate 4 and the wall close an interior I of the fermenter gas tight.

The rotatable agitator 2 that is shown in an installed position 5 includes a rotatable shaft 6 where six stirring elements 7 configured as paddles are arranged at a distance from each other. Adjacent stirring elements 7 are rotated relative to each other by 180 degrees.

The rotatable agitator 2 includes a drive 27 that is arranged at an upper end 8 of the shaft 6 and that drives the shaft 6. The drive is well known in the art and includes a motor and a transmission.

The shaft 6 includes a longitudinal axis 9 that is inclined at an angle $\alpha$ of 15 degrees relative to vertical in the illustrated installation position 5.

The ceiling device 3 of the container 1 is configured as a concrete plate and includes an elongated opening 11 that is enveloped by a frame 10 with an upper bearing and which facilitates pulling out the agitator 2. The opening 11 has a length L that corresponds approximately to a sum of a diameter d of the shaft 6 and a length L' of a paddle or slightly more. When pulling out the rotatable agitator 2 it is turned so that a paddle that passes the opening 11 is aligned with the opening 11 so that it fits through.

Figure 2:
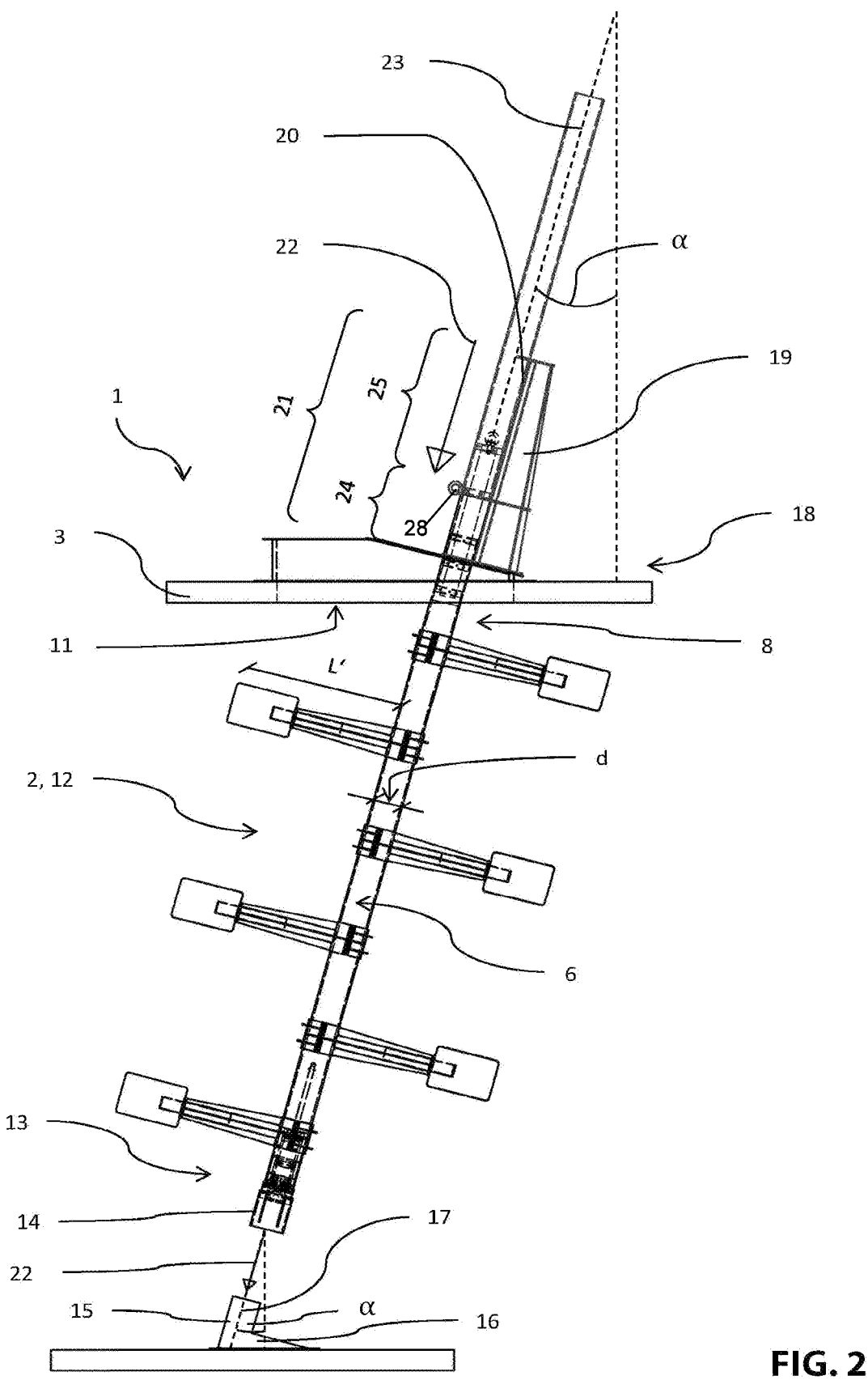
FIGS. 2 and 3 illustrate a respective side view of the container of FIG. 1 during assembly and in an installed position of the rotatable agitator.

In FIG. 2, the rotatable agitator 2 is in a mounting position 12 where it is largely inserted through the opening 11 into the fermenter. A bearing device configured as a bearing cartridge 14 fixes the shaft 6 in a lower bearing 15 wherein the bearing device is arranged at a lower end 13 of the shaft 6 wherein the bearing 15 is fixed by a bearing base 16 at the base plate 4. The lower bearing 15 is a rectangular sleeve with a longitudinal axis 17 which is also tilted at the angle $\alpha$ of 15 degrees relative to vertical. The bearing cartridge 14 is inserted into the lower bearing 15 to produce a plug in connection in which the bearing cartridge 14 cannot rotate. The shaft rotates relative to the bearing cartridge 14 that envelops it on the outside and in which the actual axial and the radial bearings are arranged. In order to retrieve the rotatable agitator the shaft 6 with the bearing cartridge 14 can be pulled out of the lower bearing 15 again. Furthermore the shaft 6 is supported in an upper bearing during operations wherein the upper bearing is arranged in a portion of the opening 11. The upper bearing is attached at a transmission cover that is in turn connected in a force transferring manner with a wall or ceiling device of the container.

A support device 19 with a contact surface 20 for the shaft 6 is arranged at a top side of the container 1 that is formed in the illustrated embodiment by the ceiling device 3 wherein the shaft 6 is already in contact with the contact surface 20 in FIG. 2.

Due to the paddles arranged at the shaft 6 the rotatable agitator 2 is initially inserted into the opening 11 in an approximately vertical direction during installation through the opening 11 and aligned according to the paddle that is arranged at the opening 11, thus rotated so that the paddle moves through the opening 11. Due to the size and the weight of the rotatable agitator 2 it is installed using a crane that is also not shown in the drawing figure. When all six paddles are in the interior I of the container 1 the agitator 2 is pivoted relative to the support device 19 so that the shaft 6 comes in contact with a section 21 with the contact surface 20 of the support device 19 which is clearly evident from FIG. 2.

In the instant embodiment, the section 21 is divided into two sections 24, 25 wherein the first section 24 is associated with the actual shaft 6 and the second section 25 is associated with an extension 23 that will be described infra.

The contact surface 20 of the support device 19 also encloses an angle $\alpha$ with the vertical so that the rotatable agitator 2 is already oriented according to the installation position 5 when the rotatable agitator 2 contacts the support device 19. Thereafter a downward movement along the contact surface 20 is performed that is indicated by two arrows 22 and the rotatable agitator 2 moves into the lower bearing 15 with its bearing device.

Figure 3:
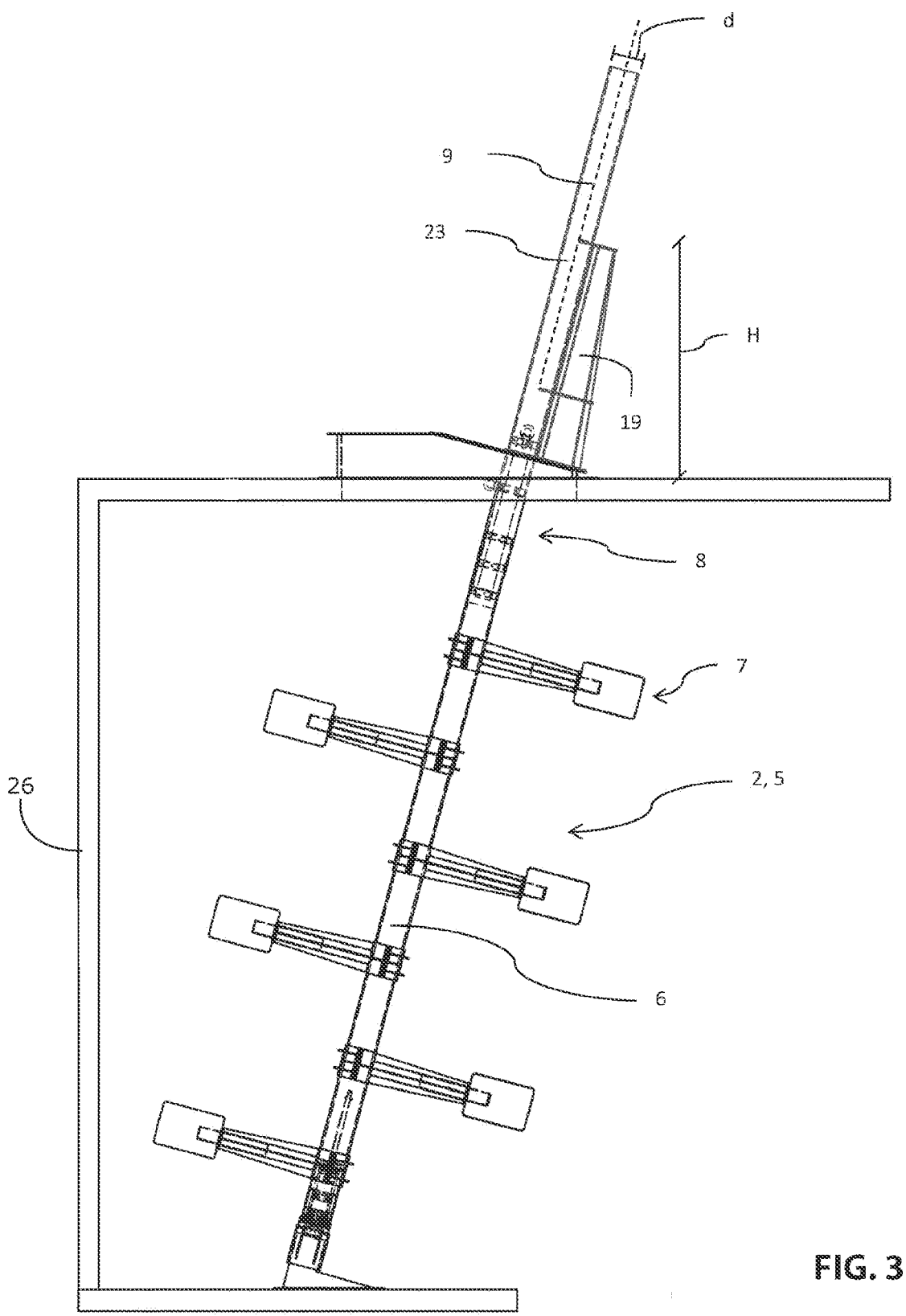

The installed position 5 of the rotatable agitator 2 is illustrated in FIG. 3 where the lower end 13 of the shaft 6 is coupled with the lower bearing 15 with the bearing cartridge 14 of the shaft 6. The rotatable agitator can be operated, this means rotated, in this position where it is supported on two sides. FIG. 3 furthermore indicates that the shaft 6 in the installed position 5 of the rotatable agitator 2 protrudes far beyond the container 1 in an upward direction and even protrudes upward beyond an elevation above the support device 19. The reason is that the shaft 6 has an extension 23 at an upper end 8 wherein the extension is connected with the shaft 6 in a form locking and disengageable manner. The extension 23 at the shaft 6 extends the section of the shaft that is in contact with the contact surface 20 of the support device 19 so that the rotatable agitator 2 can be comfortably installed. Since the extension 23 has the same diameter d in the instant embodiment as the shaft 6 it looks like the shaft 6 is configured with the respective length. Actually, the shaft 6 protrudes only marginally beyond the cover ceiling device 3 of the container 1.

When the rotatable agitator 2 is in the installed position 5 the extension 23 of the shaft 6 is disengaged so that the rotatable agitator 2 terminates approximately flush with the container. Thereafter, the drive device that is not illustrated in the drawing figures is attached at the shaft 6 and the rotatable agitator 2 is ready to operate.

As illustrated in FIGS. 1 and 3 the support device 19 includes radial supports 28 configured to fix the section 21 of the shaft at the support device 19, wherein the radial supports 28 that fix the shaft 6 in a radially and directionally fixed position facilitate an axial linear movement of the shaft 6 relative to the contact surface 20 in the radially and directionally fixed position, wherein the shaft 6 is aligned with the contact surface 20 in the radially and directionally fixed position.

REFERENCE NUMERALS AND DESIGNATIONS 1 container
2 rotatable agitator
3 ceiling device
4 base plate
5 installed position
6 shaft
7 stirring element
8 upper end of shaft
9 longitudinal axis of shaft
10 frame, upper bearing
11 opening
12 mounting position
13 lower end of shaft
14 bearing cartridge
15 bearing
16 bearing base
17 longitudinal axis
18 topside of container
19 support device
20 contact surface
21 section
22 arrow
23 extension
24 first section
25 second section
26 wall
27 drive
28 radial support
I inner cavity
L length of opening
L' length of paddle
d diameter of shaft
H height of support device
α angle

What is claimed is:

1. A container for fermenting bio-degradable substances, the container comprising:
   at least one base and at least one wall, wherein an interior of the container is enclosed by the at least one base and the at least one wall;
   at least one rotatable agitator that protrudes into the interior and is supported in an upper bearing and a lower bearing in an installed position of the at least one rotatable agitator in the container,
   wherein the at least one rotatable agitator includes a shaft that is drivable by a drive,
   wherein at least one stirring paddle Is fixed in position relative to the shaft and configured to co-rotate with the shaft so that substances arranged in the container are stirrable,
   wherein the lower bearing is arranged at the at least one base of the container and a support bearing located at a lower end of the shaft is supported in the lower bearing in the installed position of the at least one rotatable agitator,
   wherein the shaft includes a longitudinal axis that is inclined at an angle between 5 degrees and 60 degrees relative to vertical in the installed position of the at least one rotatable agitator,
   wherein a guide is arranged at an upper side of the container and includes a contact surface for at least a section of the shaft,
   wherein the lower end of the shaft of the at least one rotatable agitator is alignable with the lower bearing into an aligned position of the shaft by moving the shaft along the contact surface so that the at least one rotatable agitator is axially movable from the aligned position into the installed position, and
   wherein the contact surface is oriented parallel to the shaft in the aligned position of the shaft and in the installed position of the shaft and inclined at the angle between 6 degrees and 60 degrees relative to vertical.

2. The container according to claim 1, further comprising: a shaft extension that is connected in a disengageable manner with an upper end of the shaft.

3. The container according to claim 2,
   wherein the shaft including the shaft extension connected to the shaft protrudes beyond an upper edge of the at least one wall in the installed position, and
   wherein a section of the shaft that protrudes beyond the upper edge of the at least one wall has a length of at least 1 m.

4. The container according to claim 2,
   wherein a longitudinal axis of the shaft extension coincides with the longitudinal axis of the shaft, and
   wherein the shaft extension has a diameter that is identical to a diameter of the shaft.

5. The container according to claim 1, further comprising: a ceiling,
   wherein the at least one base, the at least one wall, and the ceiling encloses the interior of the container essentially gas tight.

6. The container according to claim 5,
wherein the ceiling includes at least one opening configured to pass the at least one rotatable agitator through, and
wherein the guide is arranged at the at least one opening.

7. The container according to claim 1, wherein the guide is connected with the container in a disengageable manner.

8. The container according to claim 1,
wherein the guide includes at least two radial supports configured to fix the section of the shaft at the guide,
wherein the at least two radial supports that fix the shaft in a radially and directionally fixed position facilitate an axial linear movement of the shaft relative to the contact surface in the radially and directionally fixed position, and
wherein the shaft is aligned with the contact surface in the radially and directionally fixed position.

* * * * *